(12) United States Patent
Braunstein et al.

(10) Patent No.: US 6,431,370 B1
(45) Date of Patent: *Aug. 13, 2002

(54) DIRECT ENZYME AGGLOMERATION PROCESS

(75) Inventors: Edit L. Braunstein, Orlando, FL (US); Nathaniel T. Becker, Hillsborough; Thomas P. Graycar, Pacifica, both of CA (US)

(73) Assignee: Genencor International, Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/590,371

(22) Filed: Jun. 8, 2000

Related U.S. Application Data

(63) Continuation-in-part of application No. 08/887,494, filed on Jul. 2, 1997, now Pat. No. 6,105,786, which is a continuation of application No. 08/379,377, filed on Jan. 27, 1995, now abandoned.

(51) Int. Cl.[7] .............................. C11D 7/42; C12S 9/00; C12N 9/00; C12N 9/54
(52) U.S. Cl. ....................... 210/392; 210/530; 435/183; 435/221; 435/816
(58) Field of Search ................................ 435/183, 221, 435/816; 210/392, 530

(56) References Cited

U.S. PATENT DOCUMENTS

| 3,773,671 A | 11/1973 | Hussain |
| 4,144,130 A | 3/1979 | Kula et al. |
| 5,814,501 A | 9/1998 | Becker et al. |

FOREIGN PATENT DOCUMENTS

| DE | DD 151 598 | 10/1981 |
| DE | 197 57 215 | 6/1999 |
| EP | 0 574 050 A1 | 12/1993 |
| GB | 1387886 | 3/1975 |
| NL | 7 104 552 | 6/1971 |
| WO | WO 96/23061 | 8/1996 |

OTHER PUBLICATIONS

International Search Report for Application No. PCT/US01/17890.

Bordier, C., "Phase Separation of Integral Membrane Proteins in Triton X–114 Solution" *The Journal of Biological Chemistry* 256(4):1604–1607 (1981).

Förster, M. et al., "Application of the Two–Phase–System 'Aqueous Solution/Triton X–114' in Protein Chemistry: Extraction of Hydrophilic Proteins by Varying Ionic Strength and the Use of Dense Sucrose Solutions" *Modern Methods in Analytical Protein Chemistry* pp. 1010–1011 abstract (1982).

Kitahara, T., et al., "Application of pluronic F68 for aqueous two–phase extraction of proteins" *Journal of Chemical Engineering of Japan* 26(2):183–188 (1993).

Terstappen, G.C., et al., "The Use of Detergent–Based Aqueous Two–Phase Systems for the Isolation of Extracellular Proteins: Purification of a Lipase from *Pseudomonas cepacia*" *Biotechnology and Applied Biochemistry* 16:228–235 (1992).

Terstappen, G.C., et al., "Protein partitioning in detergent–based aqueous two–phase systems" *Journal of Biotechnology* 28:263–275 (1993).

*Primary Examiner*—Jon P. Weber
(74) *Attorney, Agent, or Firm*—LeeAnn Gorthey

(57) ABSTRACT

Detergent formulations are prepared by directly agglomerating a fermentation broth extract, containing a detergent-type enzyme and a nonionic detergent-type surfactant, with a suitable detergent base mixture, without need for prior isolation of the enzyme.

5 Claims, No Drawings

DIRECT ENZYME AGGLOMERATION PROCESS

This application is a continuation-in-part of U.S. Ser. No. 08/887,494, filed Jul. 2, 1997, now U.S. Pat. No. 6,105,786, and a continuation of Ser. No. 08/379,377, filed Jan. 27, 1995, now abandoned which are hereby incorporated by reference in their entirety.

FIELD OF THE INVENTION

The present invention provides processes for preparing detergent formulations, by directly agglomerating an extract of a fermentation broth containing a detergent-type enzyme with a suitable detergent base mixture, without need for prior isolation of the enzyme.

BACKGROUND OF THE INVENTION

Detergent formulations in use today frequently contain enzymes, such as proteases, lipases, amylases, and cellulases, which contribute to the breakdown of soil materials. The detergent base to which the enzyme is added typically contains compounds known to be detrimental to enzyme stability, e.g., bases, such as sodium carbonate, and anionic surfactants, such as linear alkylbenzene sulfonates. Anionic surfactants, for example, are known to denature enzymes. Accordingly, enzymes incorporated into such formulations are, conventionally, separately granulated to form coated enzyme particles before addition. The coating, which typically comprises polymers such as polyvinyl alcohol, polyethylene glycol, and/or methylcellulose, serves to protect the enzyme from exposure to bases and anionic surfactants during agglomeration.

Enzyme is present in such granules at high concentration, and exposure to dusts from the granules can be hazardous to workers. Although processes for reducing dusts have been reported (see e.g. N. T. Becker et al., U.S. Pat. No. 5,814,501 (September 1998); A. G. J. Hussain, U.S. Pat. No. 3,773,671 (Nov 1973), elimination of the requirement for separate isolation and granulation of the enzyme would eliminate this hazard, as well as providing a more efficient formulation process.

SUMMARY OF THE INVENTION

The present invention provides, in one aspect, a process for preparing a detergent formulation. In accordance with the process, an aqueous fermentation broth extract is provided, in the form of a liquid or, preferably, a paste, comprising (a) a detergent-type enzyme and (b) a surfactant suitable for incorporation into such a detergent formulation. The extract is then directly agglomerated with a detergent base mixture, which is typically also in the form of a paste.

The extract may be prepared by (a) forming a mixture of an aqueous fermentation broth containing the enzyme and a detergent-type surfactant, under such conditions that the mixture undergoes a phase separation, and (b) recovering a phase containing the enzyme and the surfactant. In one embodiment, the mixture of step (a) further includes a salt having a metal cation and a halide or polar oxygenated anion. In another embodiment, the conditions inducing phase separation include heating the mixture to a temperature above its cloud point.

The detergent-type surfactant is preferably selected from the group consisting of an alkyl polyether alcohol, an alkylphenol polyether alcohol, an ethoxylated fatty alcohol, a higher fatty acid alkanolamide or alkylene oxide adduct thereof, and a fatty acid glycerol monoester, and is more preferably an alkyl polyether alcohol, an alkylphenol polyether alcohol, or an ethoxylated fatty alcohol.

These and other objects and features of the invention will become more fully apparent in the following detailed description of the invention.

DETAILED DESCRIPTION OF THE INVENTION

I. Definitions

The terms below have the following meanings unless indicated otherwise.

As used herein, a "detergent-type enzyme" refers to any enzyme which may be useful in a cleaning product such as a laundry detergent, a hard surface cleaner, a personal care cleaning product, a dishcare product, etc. Such enzymes include, but are not limited to, proteases, cellulases, amylases, endoglycosidases, lipases, peroxidases, lactases, and catalases. Specifically useful enzymes include alkaline proteases such as PURAFECT® or PURAFECT® OxP (both commercially available from Genencor International, Inc.), SAVINASE™ (Novo Industries), protein engineered enzymes such as Protease 899 (Genencor International, Inc.), DURAZYM™ (a protease having +195 and +222 mutations, Novo Nordisk A/S), and MAXAPEM™ (a protease having a +222 mutation, Gistbrocades); amylases such as SPEZYME® (Genencor International, Inc.) or protein engineered amylases such as described in U.S. Pat. No. 5,824,532 (C. C. Barnett et al., October 1998); cellulases or cellulase components, such as DENIMEX™ (Novo Nordisk A/S); and endoglycosidases, such as those described in U.S. Pat. No. 5,238,843 (R. S. Carpenter et al., August 1993) and U.S. Pat. No. 5,258,304 (R. S. Carpenter et al., November 1993).

A "detergent-type surfactant" is one which is suitable for incorporation into a detergent formulation and is effective in enzyme extractions as described herein. For the latter purpose, nonionic surfactants should be used. Detergent-type surfactants are described in *McCutcheon's Emulsifiers and Detergents* 1999: North American Edition, Vol. 1, McCutcheon Div., MC Publishing Co., 1999, a standard catalog of commercial surfactants, and in Schick, M. J. (Ed.), *Nonionic Surfactants*, Marcel Dekker, 1987. Such surfactants suitable for use in the present processes include, for example, alkyl polyether alcohols, alkylphenol polyether alcohols, such as TRITON® X-100, X-165, X-305 or X-405 (Rohm & Haas), ARMUL® 930 (Witcho Corp.), ALKA SURF® NP-15 (Rhone Poulenc), CARSONON® N-30 (Lonza, Inc.), and CEDEPAL® CO-730 (Stepan Canada, Inc.); and alcohol ethoxylates, such as NEODOL® 91-6, 91-8, 23-6.5, 25-12, 45-13 or 25-20 (Shell). In this case, "alkyl" refers to a linear or branched hydrocarbon chain having 6 to 20 carbon atoms, and preferably from 8 to 16 carbon atoms. Other nonionic detergent-type surfactants include higher fatty acid alkanolamides or alkylene oxide adducts thereof and fatty acid glycerol monoesters.

A "fatty acid" or "fatty alcohol" includes a carbon chain, preferably a linear chain, having at least 8 carbon atoms, and preferably between 8 and 24 carbon atoms.

II. Enzyme Extraction Methods

Many enzymes can be produced in quantity by the culturing of certain organisms (yeast, bacteria, fungi) in appropriate nutrient media under suitable conditions. After culturing or fermenting the organisms to produce the desired enzyme, the enzyme is recovered from the fermentation broth. Whole fermentation broth containing enzyme fermentation products, either extracellular or intracellulat, as well as cells and/or cell fragments, which are collectively referred to as "cellular debris," can be used for extraction without further processing. Alternatively, the fermentation broth may first be clarified, by known methods such as ultrafiltration, to remove all or substantially all cellular debris. When whole fermentation broth is used, the broth may be diluted prior to extraction, to reduce the total solids percentage and the viscosity and/or conductivity of the broth.

Many recovery processes for biological/fermentation products have been developed. Any of these which incorporates at least one nonionic detergent-type surfactant, such that an extract containing the surfactant and enzyme can be recovered, may be used in the method of the invention.

A general method of recovery of enzymes from intact cells and cell fragments, termed "affinity partitioning", employs the formation of multiple, distinct phases in a common solvent upon addition of materials, typically hydrophilic oligomers or polymers and/or salts, which produce immiscible phases when in solution. For efficient separation, the product to be extracted has a selective affinity for one phase over the other.

Isolation of enzymes by partitioning of aqueous systems containing a combination of hydrophilic polymers has been described, for example, in U.S. Pat. No. 4,144,130 (M. R. Kula etal., 1979) and U.S. Pat. No. 4,743,550 (K. P. Ananthapadmanabhan et al., May 1988). Suitable combinations include PEG (polyethylene glycol) in combination with dextran, hydroxypropyl dextran, alkoxy PEG, polyvinyl alcohol, polyvinyl pyrrolidone, starch, or glycogen.

The present inventors have described a method of extracting hydrophobic proteins, which include many detergent-type proteins, in PCT Publication No. WO 96/23061, which corresponds to parent U.S. application Ser. No. 08/379,377. In this method, particularly suitable for the present processes, a whole or clarified fermentation broth is mixed with a salt and a nonionic detergent-type surfactant (as defined above) to form a two-phase system. The enzyme collects in the surfactant-rich phase, while undesired by-products, such as cellular debris, secondary enzymes, carbohydrates, etc., collect in the salt-rich phase.

Salts used in this process are preferably those wherein the cation is a monovalent or divalent metal ion, e.g. sodium, potassium, magnesium, ammonium, aluminum or calcium, and the anion is a polar oxygenated ion, such as sulfate, carbonate, phosphate, acetate, formate, nitrate or citrate, or a halide, such as chloride, bromide or iodide. Mixtures of salts may also be used. Preferred salts include sodium sulfate, sodium phosphate, sodium chloride and sodium formate. The salt(s) and surfactant are added to the fermentation broth (whole or clarified) at a temperature from about room temperature to about 40° C. The addition of the salt and surfactant can be made over a broad pH range (2–10), depending on the nature of the enzyme to be recovered. The pH, temperature and pressure of the system are maintained at a level which optimizes separation, as long as denaturation or other degradation of the enzyme does not occur.

After addition of the salt and surfactant, the fermentation broth typically separates into two phases; a third, interfacial phase may also form. Any such interfacial phase is generally treated as part of the top (surfactant-rich) phase, which includes the desired protein. Phase separation can occur simply upon settling of the mixture, or it may be achieved by centrifugation, in accordance with known methods.

In another separation method, termed cloud point extraction, phase separation occurs upon raising the temperature of an aqueous system containing a nonionic surfactant. This process is described, for example, in G. C. Terstappen et al., *J. Biotechnology* 28:263–275 (1993) and in Terstappen et al., *Biotechn. Appl. Biochem.* 16(3):228–235 (1992), using polyoxyethylene tert-octyl phenyl ethers (TRITON® X-100 and X-114) and polyoxyethylene n-tetradecyl ether (C14E06, Henkel KGAA), respectively. In a typical procedure, about 1% weight/volume surfactant is added to an aqueous mixture containing the protein, and the resulting mixture is maintained for two hours at about 2° C. above the cloud point, allowing phase separation to take place. TRITON® X-114, having a cloud point of about 28° C., is a preferred surfactant for this method.

IV. Incorporation of Extract into Detergent Formulation

An extract containing a detergent-type surfactant and a detergent-type enzyme, preferably obtained by one of the extraction methods described above, is collected or recovered by methods known to those skilled in the art, including, for example, centrifugation. The surfactant/enzyme phase is then incorporated directly into the desired detergent base formulation. For direct agglomeration into solid or paste detergent formulations, extraction of the enzyme is preferably carried out so as to result in a highly viscous material, which can typically be achieved by adjusting the concentration of the mixture or the amount of surfactant added. A representative procedure, in which a paste-like extract was obtained by reducing the amount of surfactant, is described below in Example 3.

Detergent or cleaning product formulations include, but are not limited to, any industrial or consumer cleaning product such as laundry products, hard surface cleaners, laundry pre-treatment products, dishcare products, personal hygiene products, etc. The formulation will typically contain anionic, cationic and nonionic surfactants, and may also include components such as antioxidants, alkanolamines, polycarboxylate detergent builders, antiredeposition agents, suds regulators, bactericides, dyes, fragrances, brighteners, etc. The skilled artisan is familiar with different formulations which can be used as cleaning compositions. Such formulations are described, for example, in U.S. Pat. No. 4,404,128 (Anderson, September 1983), U.S. Pat. No. 4,261,868 (J. Hora et al., April 1981) and U.S. Pat. No. 4,507,219 (Hughes, March 1985), which are incorporated herein by reference.

As described below, the direct agglomeration process was carried out successfully using the enzyme subtilisin, with no detectable degradation of the enzyme. The process has the cost and processing advantages of obviating the need for separate granulation of enzyme and handling of a granulated enzyme admix. Commercial agglomerators for handling surfactant pastes can easily handle the enzyme-surfactant paste (or liquid). Further, the concentration of enzyme in the agglomerated detergent is 10–200 times lower than that found in commercial enzyme granules, so the risk of exposure to sensitizing enzyme dusts is reduced.

Without wishing to be limited by mechanism, it is hypothesized that extraction of the enzyme by a nonionic surfactant may serve to coat or otherwise shield it from chemical attack. In view of the successful application of direct agglomeration of such extracts in detergent formulations, it is expected that similar methods could also be used in other formulation processes, e.g. in the pharmaceutical industry, which conventionally employ separately granulated and coated proteins.

EXAMPLES

The following examples are for illustrative purposes only and are not intended to limit the scope of the present invention.

Examples 1 and 2 illustrate a salt/surfactant extraction of a protease from a fermentation broth. Similar procedures were used to extract Protease 899 (using TRITON® X-405), PURAFECT® (using NEODOL® 91-6), and LUMAFAST® (using TRITON® X-305 and X-405), as described in co-owned PCT Publication No. 96/23061.

Example 1

A fermentation of Protease 2 (a subtilisin, as described in U.S Pat. No. 5,185,258) expressed in *B. subtilis* was carried out. The fermentation broth was clarified by flocculation of the biomass and filtration through a rotary vacuum drum filter (RVDF). A 100 ml sample of the filtrate was adjusted to pH 7 with formic acid, and 15 grams of sodium sulfate and 10 grams of sodium chloride were added. The mixture was warmed to 25° C. and stirred for about 1 hour to dissolve all of the salt. TRITON® X-100 (octylphenol polyether alcohol, Rohm & Haas) (10 mL, or 10% of initial filtrate volume) was added, and the mixture was stirred for about 15 minutes. The mixture was separated into two phases (a top phase rich in the surfactant and a bottom phase rich in salts) by centrifugation (IEC Centra-P Centrifuge) at about 3000 g for about 15 minutes, and the phases were assayed for subtilisin activity.

The following parameters were calculated: the volume split (volume of top phase/volume of bottom phase) was 0.2; the partition coefficient (enzyme concentration in top phase/enzyme concentration in bottom phase) was 442; the concentration factor (enzyme concentration in top phase/original concentration) was 4.7, and the yield (total enzyme recovered in top phase/initial quantity of enzyme) was 93%.

Example 2

The extraction procedure described in Example 1 above, was repeated, substituting 10 mL of NEODOL® 91-6 (ethoxylated alcohol, C9-11; Shell) for the TRITON® X-100 surfactant, with the following results: Volume split 0.22; Partition coefficient 57; Concentration factor 4.66; Yield 100%.

Example 3

This example illustrates direct agglomeration of an enzyme extract into a detergent formulation.

A surfactant extract of alkaline protease is prepared by the process described in Example 2, except that the extraction is run using 5–10%, preferably about 5–7%, of the NEODOL® surfactant, such that the extract has the consistency of a paste. The extract paste, having a protease concentration of 4% w/w, was then added to a high shear agglomerator (such as made by Lodige or Shugi) together with a base detergent paste mixture containing anionic surfactants (linear alkylbenzene sulfonate, alkyl sulfate, alkyl ethoxy sulfate) and nonionic surfactants (alkyl ethoxylated alcohols). The extract is typically added at about 1% of the weight of the base detergent mixture, but could be added at from 0.1% to 10% of this level.

After agglomeration, by operating the blades at high speed for 0.25 to 10 minutes, the enzyme-containing surfactant agglomerate was removed as a flowable, granular detergent powder.

A similar process was carried out using the enzyme subtilisin. No significant loss of enzyme activity was observed up to and after several weeks storage at elevated temperature and humidity.

While the invention has been described with reference to specific methods and embodiments, it will be appreciated that various modifications may be made without departing from the invention.

It is claimed:

1. A process for preparing a detergent formulation, comprising
    (a) forming a mixture of (i) an aqueous fermentation broth containing a detergent-type enzyme, selected from the group consisting of a protease, a cellulase, an amylase, an endoglycosidase, a lipase, a peroxidase, a lactase, and a catalase, and (ii) a surfactant, selected from the group consisting of an alkyl polyether alcohol, an alkylphenol polyether alcohol, an ethoxylated fatty alcohol, a higher fatty acid alkanolamide or alkylene oxide adduct thereof, and a fatty acid glycerol monoester, under such conditions that the mixture undergoes a phase separation;
    (b) recovering a phase containing the enzyme and the surfactant, thereby providing an aqueous fermentation broth extract, in the form of a liquid or paste; and
    (c) directly agglomerating said extract with a detergent base mixture.

2. The process of claim 1, wherein the mixture of step (a) further includes a salt having a metal cation and a halide or polar oxygenated anion.

3. The process of claim 1, wherein the conditions include heating the mixture to a temperature above its cloud point.

4. The process of claim 1, wherein the surfactant is selected from the group consisting of an alkyl polyether alcohol, an alkylphenol polyether alcohol, and an ethoxylated fatty alcohol.

5. The process of claim 1, wherein the extract is in the form of a paste.

* * * * *